United States Patent [19]

Furlenmeier et al.

[11] Patent Number: 5,055,572

[45] Date of Patent: Oct. 8, 1991

[54] CEPHALOSPORIN DERIVATIVES

[75] Inventors: André Furlenmeier, Basle; Erwin Götschi; Paul Hebeisen, both of Reinach; Werner Hofheinz, Bottmingen; Helmut Link, Basle, all of Switzerland

[73] Assignee: Hoffmann-La Roche Inc., Nutley, N.J.

[21] Appl. No.: 179,199

[22] Filed: Apr. 8, 1988

[30] Foreign Application Priority Data

Apr. 10, 1987 [CH] Switzerland ............... 1407/87
Apr. 30, 1987 [CH] Switzerland ............... 1657/87
Jun. 26, 1987 [CH] Switzerland ............... 2414/87

[51] Int. Cl.$^5$ ............ C07D 501/36; A61K 31/545
[52] U.S. Cl. ................... 514/206; 540/226; 540/227
[58] Field of Search ............ 540/225, 226, 227; 514/206

[56] References Cited

U.S. PATENT DOCUMENTS 4,888,332 12/1989 Ohnishi et al. .............. 540/227

FOREIGN PATENT DOCUMENTS 0150507 7/1985 European Pat. Off.
0189287 7/1986 European Pat. Off.

Primary Examiner—Nicholas S. Rizzo
Attorney, Agent, or Firm—George M. Gould; Bernard S. Leon; George W. Johnston

[57] ABSTRACT

Acyl derivatives of the formula

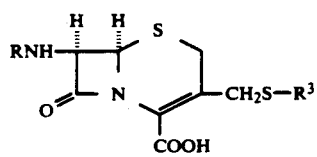

in which R is an acyl group, excluding those acyl groups of the formula

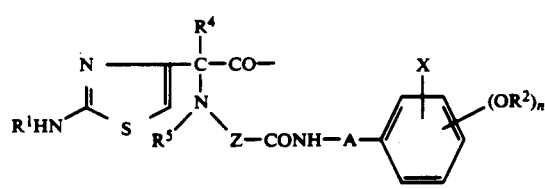

in which A is a group of the formulae —NHCO—, —NHCONHCO—, —NHCOCH=CH—,

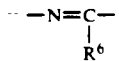

wherein $R^6$ is hydrogen or lower alkyl; $R^1$ and $R^2$ are hydrogen or a protecting group, X is hydrogen, halogen, lower alkoxy, nitro or —$OR^2$, n is 1 or 2, $R^4$ and $R^5$ are hydrogen or together represent an additional bond and Z is a direct bond or carbonyl (where $R^4$ and $R^5$ both represent hydrogen) or a group of the formula —O—B— (where $R^4$ and $R^5$ together represent an additional bond) in which B is a straight-chain, branched or cyclic lower alkylene;

and wherein $R^3$ is a substituted bicyclic group of the formulae

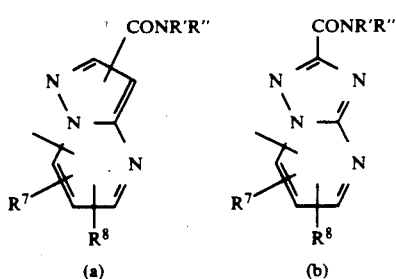

(a)     (b)

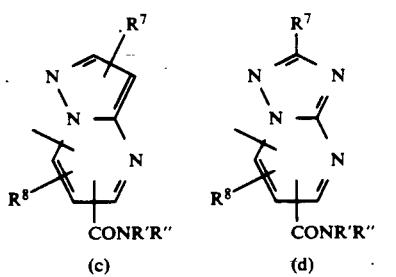

(c)     (d)

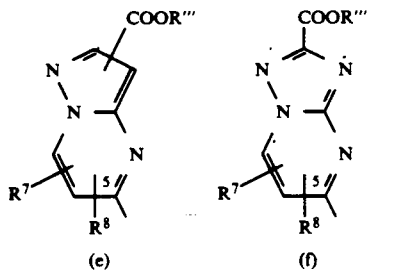

(e)     (f)

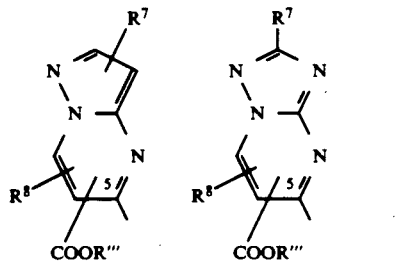

(g)     (h)

(Abstract continued on next page.)

wherein $R^7$ and $R^8$ are independently hydrogen, lower alkyl or trifluoromethyl or, in formulae (a), (b), (e) and (f) together represent alkylene with 3 or 4 carbon atoms, and R′, R″ and R‴ are independently hydrogen, lower alkyl or lower cycloalkyl; wherein compounds of formula I in which $R^4$ and $R^5$ together represent an additional bond are present in the syn-isomeric form or as a mixture with the anti-isomeric form in which the syn-isomeric form predominates, as well as readily hydrolyzable esters and salts of these compounds and hydrates of the compounds of formula I or of their esters and salts.

These compounds are useful as antibiotics.

19 Claims, No Drawings

CEPHALOSPORIN DERIVATIVES

SUMMARY OF THE INVENTION

The present invention is concerned with acyl derivatives, and more specifically with cephalosporin derivatives of the formula

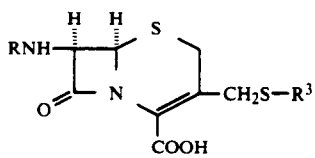

in which R is an acyl group, excluding the acyl groups of the formula

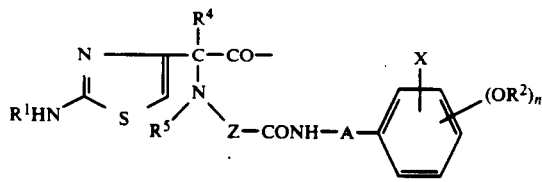

in which A is a group of the formulae —NHCO—, —NHCONHCO—, —NHCOCH=CH—,

wherein $R^6$ is hydrogen or lower alkyl, $R^1$ and $R^2$ are hydrogen or a protecting group, X is hydrogen, halogen, lower alkoxy, nitro or —$OR^2$, n is 1 or 2, $R^4$ and $R^5$ are hydrogen or together represent an additional bond, and Z is a direct bond or carbonyl (where $R^4$ and $R^5$ are hydrogen) or a group of the formula —O—B— (where $R^4$ and $R^5$ together represent an additional bond) in which B is a straight-chain, branched or cyclic lower alkylene; and wherein $R^3$ is a substituted bicyclic group of the formulae

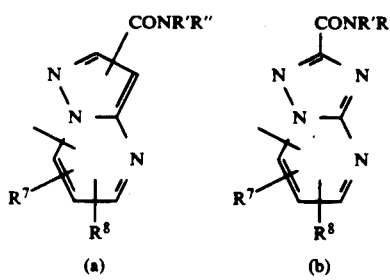

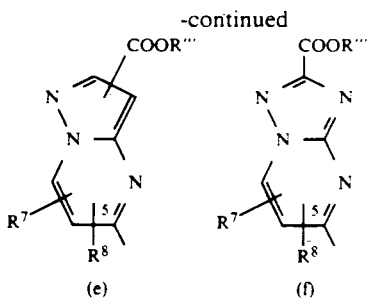

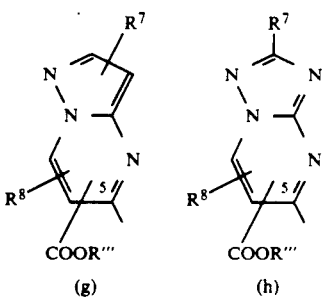

wherein $R^7$ and $R^8$ are independently hydrogen, lower alkyl or trifluoromethyl or in formulae (a), (b), (e) and (f) together represent alkylene with 3 or 4 carbon atoms, and R', R" and R'" are independently hydrogen, lower alkyl or lower cycloalkyl, as well as readily hydrolyzable esters and salts of these compounds and hydrates of the compounds of formula I or of their esters and salts.

Excluded from the present invention are the compounds of the formula

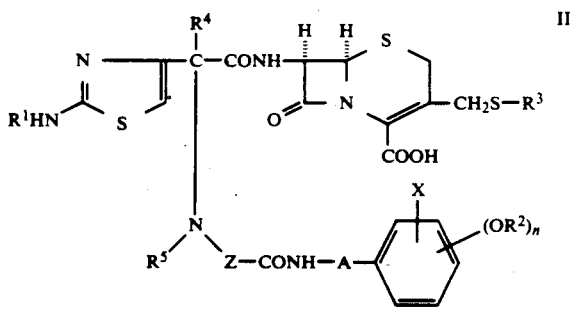

wherein $R^1$-$R^5$, A, Z and n are as defined above, as well as the readily hydrolyzable esters and salts of these compounds and hydrates of the compounds of formula II or of their esters and salts.

The present invention thus encompasses those acyl derivatives of formula I in which R is an acyl group other than those of formula II, as well as readily hydrolyzable esters and salts of the these compounds and hydrates of such compounds of formula I or of their esters and salts.

The compounds of this invention can be formulated into pharmaceutical compositions and are useful as antibacterial agents to treat bacterial infections in a host. Such pharmaceutical compositions and method of treating bacterial infections therapeutically constitute further facets of this invention.

DETAILED DESCRIPTION OF THE INVENTION

A sub-group of such compounds in accordance with the invention are those of the formula $$R^9-\underset{\underset{OR^{10}}{\overset{\|}{N}}}{C}-CONH-\overset{H}{\underset{O}{C}}-\overset{H}{\underset{N}{C}}\overset{S}{\underset{COOH}{\diagdown}}CH_2S-R^3 \quad Ia$$

in which $R^3$ has the same meaning as above, $R^9$ is an optionally substituted 5- or 6-membered heterocyclic group with 1-4, preferably 1 or 2, hetero atoms such as N, O and/or S, and $R^{10}$ is hydrogen, lower alkanoyl, lower alkyl, lower alkenyl, lower cycloalkyl, lower cycloalkenyl or lower alkyl substituted by carboxy, carbamoyl, lower alkoxycarbonyl or lower alkanoyl or $R^{10}$ is a group of the formulae

—P—Q

—P—CO—Q

—P—CO—NH—NH—CO—Q$^1$ wherein P is lower alkylene or lower cycloalkylene, Q is one of the groups (i) a benzene ring substituted with $(OR^{11})_2$, $R^{12}$, $R^{13}$ (k) HN—, —OR$^{11}$, =O wherein $R^{11}$ is hydrogen, lower alkanoyl or tri(lower alkyl)-silyl, $R^{12}$ is hydrogen, —OR$^{11}$, lower alkoxy, halogen, —OCOR$^{14}$, —OCOOR$^{14}$, —N(R$^{14}$)$_2$, —NH—COR$^{14}$, —NHCOOR$^{14}$, —COR$^{14}$, —SR$^{14}$, —SOR$^{14}$, SO$_2$R$^{14}$, —SO$_3$H, —COOR$^{14}$, —CON(R$^{14}$)$_2$ or nitro, is hydrogen or halogen and $R^{14}$ is hydrogen or lower alkyl, wherein in group (i) the two —OR$^{11}$ groups are present in the 2,3- or 3,4-position; and Q$^1$ is one of the groups (k) and (l), as well as readily hydrolyzable esters and salts of these compounds and hydrates of the compounds of formula Ia or of their esters and salts.

The compounds of formula Ia are present in the synisomeric form or as a mixture with the anti-isomeric form in which the syn-isomeric form predominates.

Examples of 5- or 6-membered heterocyclic groups represented by $R^9$ are thienyl, furyl, oxazolyl, pyrazolyl, pyridinyl, pyrazinyl, thiazolyl, pyrimidinyl, thiadiazolyl. Examples of substituents on the ring in these heterocyclic groups are: halogen, hydroxy, nitro, amino, cyano, trifluoromethyl, lower alkyl and lower alkoxy.

2-Amino-4-thiazolyl and 5-amino-3-thiadiazolyl are preferred as the heterocyclic group ($R^9$).

"Lower alkyl" and "lower alkenyl" are straight-chain and branched hydrocarbon chains with 1-7, especially 1-4, carbon atoms, for example, methyl, ethyl, n-propyl, isopropyl, t-butyl, vinyl, allyl, 2-butenyl, or the like. Modified groups such as lower alkoxy (lower alkyl-O), lower alkanoyl (lower alkyl-CO—), lower alkoxycarbonyl (lower alkyl-OCO—) and lower alkanoyloxy (lower alkyl-COO—) have a similar number of carbon atoms, also in combinations such as lower alkanoyloxyalkyl. Lower cycloalkyl and lower cycloalkenyl have 3-7 carbon atoms such as, for example, cyclopropyl, cyclobutyl, cyclohexyl, methyl-cyclopropyl and cyclohexenyl. "Lower alkylene" is as used throughout this disclosure to be understood similarly to "lower alkyl" as having 1-7, especially 1-4, carbon atoms, for example, the following:

$$-CH_2-, \quad -CH_2-CH_2-, \quad -\underset{CH_3}{\overset{|}{CH}}-, \quad -\underset{C_2H_5}{\overset{|}{CH}}-,$$

$$-\underset{C_3H_7}{\overset{|}{CH}}- \quad -\underset{CH_3}{\overset{|}{\underset{CH_3}{C}}}- \quad -CH_2-\underset{CH_3}{\overset{|}{\underset{CH_3}{C}}}-$$

"Lower cycloalkylene" and "cyclic lower alkylene" are intended to mean, similarly to "lower cycloalkyl", alkylene having 3-7 carbon atoms, for example, the following:

cyclopropylene, cyclobutylene, cyclopentylene, methylcyclopropylene structures

"Halogen" refers to all of the forms: chlorine, fluorine, bromine and iodine, especially chlorine.

Preferred groups represented by $R^{10}$ are:

Methyl, allyl, carboxymethyl, carbamoylmethyl, 1-carboxy-1-methylethyl, pivaloyl as well as the groups

—P$^1$—Q

—P$^1$—CO—Q

—P$^1$—CO—NH—NH—CO—Q$^1$ in which Q has the same meaning given above and p$^1$ is the group —CH$_2$— or $$-\underset{CH_3}{\overset{\overset{CH_3}{|}}{C}}-,$$

especially the groups

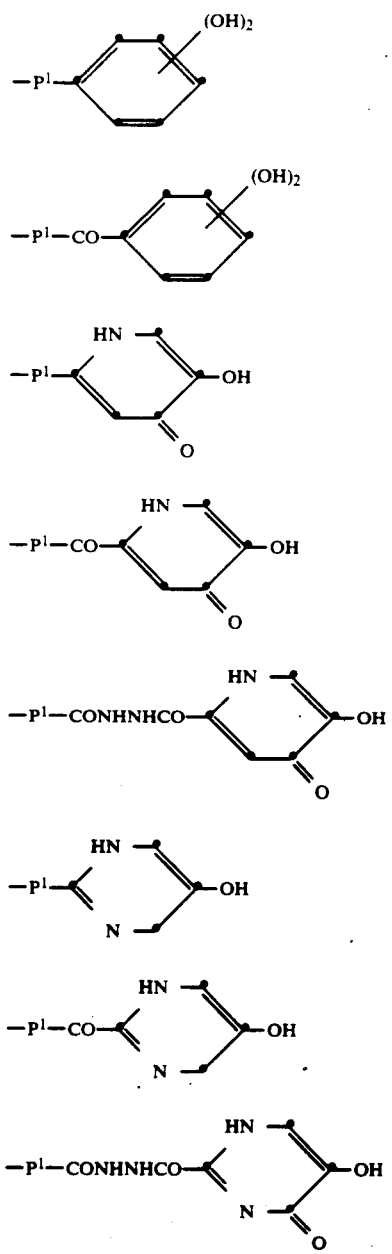

wherein $p^1$ has the same meaning given above and the two hydroxy groups denoted as $(OH)_2$ are present in 2,3- or 3,4-position.

The bicyclic groups (a)–(d) are preferably linked to the rest of the molecule via position ring 5, as follows:

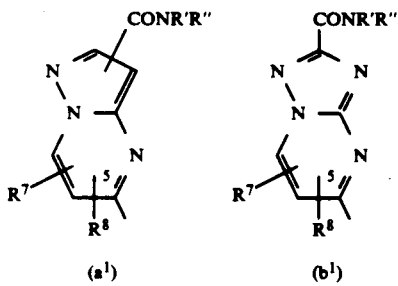

-continued

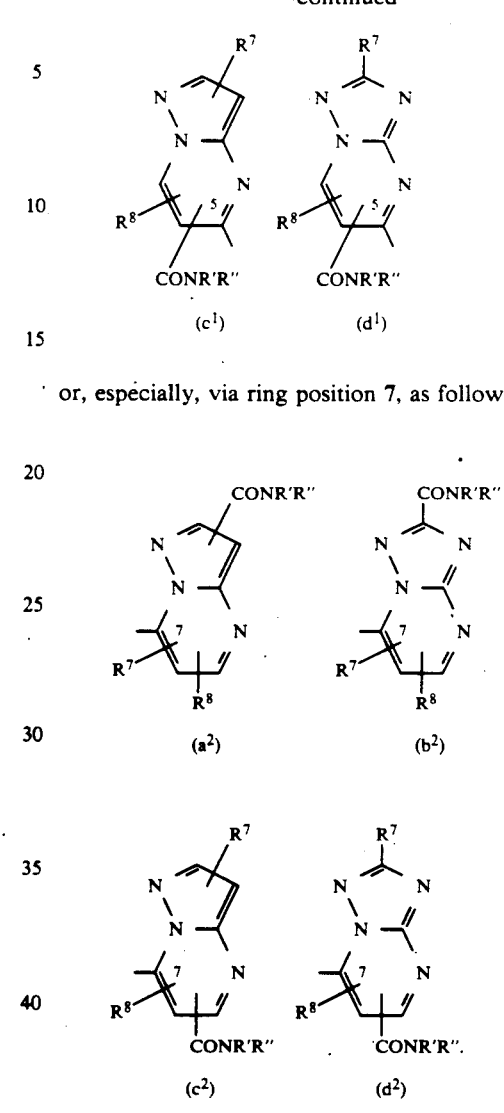

or, especially, via ring position 7, as follows:

The substituent —CONR'R" of group (a) and the substituent —COOR''' of group (e) are preferably situated in ring position 3, as follows:

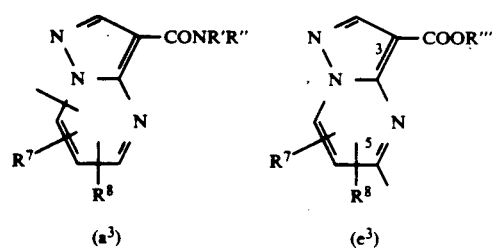

A preferred sub-group of compounds in accordance with the invention are those in which $R^3$ is a substituted bicyclic group of the formulae

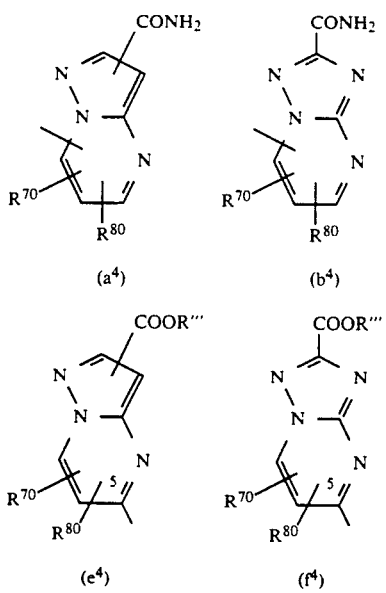

(a⁴)   (b⁴)

(e⁴)   (f⁴)

wherein R⁷⁰ and R⁸⁰ are independently hydrogen, methyl or trifluoromethyl or together represent alkylene with 3 or 4 carbon atoms and R''' is hydrogen or methyl.

Preferred groups represented by R³ are the following:

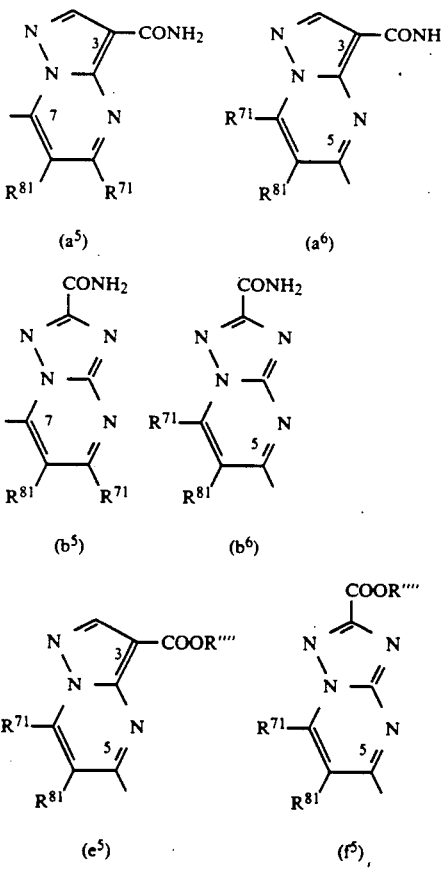

(a⁵)   (a⁶)

(b⁵)   (b⁶)

(e⁵)   (f⁵)

wherein R⁷¹ is methyl or trifluoromethyl and R⁸¹ is hydrogen or R⁷¹ and R⁸¹ together represent tetramethylene and R'''' is hydrogen or methyl.

Especially preferred groups represented by R³ are the following:

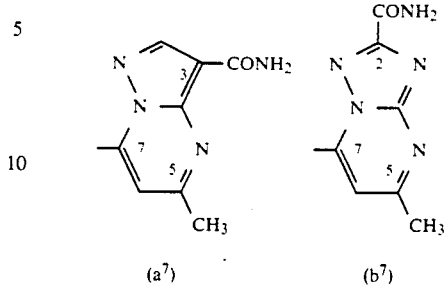

(a⁷)   (b⁷)

Salts of the compounds of formula I are pharmaceutically compatible salts and can be salts with bases or with acids. Salts with bases are, for example, alkali metal salts such as the sodium and potassium salt; the ammonium salt; alkaline earth metal salts such as the calcium salt; salts with organic bases such as salts with amines, for example, salts with diisopropylamine, benzylamine, dibenzylamine, triethanolamine, triethylamine, N,N-dibenzylethylenediamine, N-methylmorpholine, pyridine, piperazine, N-ethyl-piperidine or procaine. The compounds of formula I also form addition salts with organic or inorganic acids. Examples of such salts are hydrohalides, for example, hydrochlorides, hydrobromides, hydroiodides, as well as other mineral acid salts such as sulphates, nitrates, phosphates and the like, alkyl- and mono-arylsulphonates such as ethanesulphonates, toluenesulphonates, benzenesulphonates and the like, and also other organic acid salts such as acetates, tartrates, maleates, citrates, benzoates, salicylates, ascorbates, and the like.

Readily hydrolyzable esters of the compounds of formula I include compounds of formula I in which the carboxy group is present in the form of a readily hydrolyzable ester group. Examples of such esters are the lower alkanoyloxyalkyl esters, for example, the acetoxymethyl, pivaloyl-oxymethyl, 1-acetoxyethyl and 1-pivaloyloxyethyl ester; the lower alkoxycarbonyloxyalkyl esters, for example, the methoxy-carbonyloxymethyl, 1-ethoxycarbonyloxyethyl and 1-isopropoxycarbonyloxyethyl ester; the lactonyl esters, for example, the phthalidyl and thiophthalidyl ester; the lower alkoxy-methyl esters, for example, the methoxymethyl ester; and the lower alkanoylaminomethyl esters, for example, the acetamidomethyl ester. Other esters, for example, the benzyl and cyanomethyl ester, can also be used. Additional carboxy groups which may be present in a compound of formula I can also form the above readily hydrolyzable esters.

The compounds of formula I, including their salts and readily hydrolyzable esters, can be hydrated. The hydration can take place in the course of preparation or can occur gradually as a consequence of hygroscopic properties of an initially anhydrous product.

Preferred products are the following:

(6R,7R)-7-[(Z)-2-(2-Amino-4-thiazolyl)-2-(methoxyimino)acetamido] -3-[[[2-carbamoyl-5-methyl-s-triazolo[1,5-a]-pyrimidin -7-yl]thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[(t-butoxycarbonyl)methoxy]imino]acetamido]-3-[[[2-carbamoyl-5-methyl-s-triazolo [1,5-a]pyrimidin-7-yl]thio]methyl]-8-oxo-5-thia-1-azabicyclo [4.2.0]oct-2-ene-2-carboxylic acid, (6R,7R)-7-[(Z)-2-(2-amino-4-thiazolyl)-2-[(pivaloyloxy)imino]acetamido]-3-[[[2-carbamoyl-5-methyl-s-triazolo[1,5-a pyrimidin-7-yl]thio]methyl]-8-oxo-5-thia-1-azabicyclo[4.2.0]oct-2-ene-2-carboxylic acid, (6R,7R)-7-[(Z)-2-(2-amino-4-thiazolyl)-2-[[1-(t-butoxycarbonyl) -1-methylethoxy]imino]acetamido]-3-[[[2-carbamoyl-5-methyl-s-triazolo [1,5-a]pyrimidin-7-yl]thio]methyl]-8-oxo-5-thia-1-azabicyclo [4.2.0]oct-2-ene-2-carboxylic acid, (6R,7R)-7-[(Z)-2-(2-amino-4-thiazolyl)-2-[(carboxymethoxy)imino]acetamido]-3-[[(2-carbamoyl-5-methyl-s-triazolo [1,5-a]]pyrimidin-7-yl)thio]methyl]-8-oxo-5-thia-1-a azabicyclo[4.2.0]oct-2-ene-2-carboxylic acid, (6R,7R)-7-[(Z)-2-(2-amino-4-thiazolyl)-2-[1-(carboxy-1-methylethoxy)imino]acetamido]-3-[[[2-carbamoyl-5-methyl-s-triazolo[1,5-a]pyrimidin-7-yl]thio]methyl]-8-oxo-5-thia-1-azabicyclo [4.2.0]oct-2-ene-2-carboxylic acid, (6R,7R)-7-[(Z)-2-(2-amino-4-thiazolyl)-2-[(carbamoylmethoxy)imino]acetamido]-3-[[(2-carbamoyl-5-methyl-s-triazolo [1,5-a]pyrimidin-7-yl)thio]methyl]-8-oxo-5-thia-1-azabicyclo [4.2.0]oct-2-ene-2-carboxylic acid, (6R,7R)-7-[(Z)-2-(2-amino-4-thiazolyl)-2-[[1-[3-[(1,4-dihydro -5-hydroxy-4-oxo-2-pyridyl) carbonyl]carbazoyl]-1-methylethoxy]imino]acetamido]-3-[[(2-carbamoyl-5-methyl-s-triazolo [1,5-a]pyrimidin-7-yl)thio]methyl]-8-oxo-5-thia-1-azabicyclo [4.2.0]oct-2-ene-2-carboxylic acid, (6R,7R)-7-[(Z)-2-(2-amino-4-thiazolyl)-2-[[(1,4-dihydro -5-hydroxy-4-oxo-2-pyrimidinyl) methoxy]imino]acetamido]-3-[[(2-carbamoyl-5-methyl-s-triazolo[1,5-a]pyrimidin-7-yl)thio] methyl]-8-oxo-5-thia-1-azabicyclo[4.2.0]oct-2-ene-2-carboxylic acid, as well as salts of these compounds.

The above compound in accordance with this invention can be prepared as follows:

(a) reacting a compound of the formula

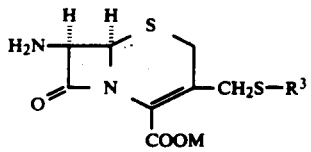

in which $R^3$ has the same meaning given above and M is hydrogen or an ester protecting group, with an acylating agent and, if desired, cleaving off any protecting group, or (b) reacting a compound of the formula

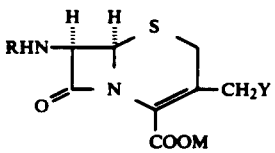

in which R and M have the same meanings given above and Y is a leaving group, with a compound of the formula

HSR³                V in which $R^3$ is as defined above, and, if desired, cleaving off any protecting groups, or (c) for the preparation of compounds of formula I in which R has the formula

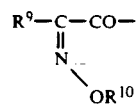

wherein $R^9$ and have the meanings given above, reacting a compound of the formula

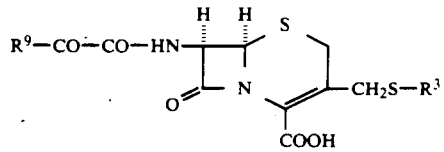

wherein $R^3$ and $R^9$ are as defined above, with a salt of a compound of the formula

NH₂OR¹⁰            VII wherein $R^{10}$ has the meaning given above, or (d) for the preparation of a readily hydrolyzable ester of a compound of formula I, subjecting a carboxylic acid of formula I to an appropriate esterification, or (e) for the preparation of salts and hydrates of a compound of formula I or of hydrates of these salts, converting a compound of formula I into a salt or hydrate or into a hydrate of this salt.

Any reactive groups in the starting compounds used above can be protected, if desired. Thus, for example, phenolic hydroxy groups can be protected by acetyl, trimethylsilyl or tetrahydropyranyl and amino groups can be protected by protecting groups which are cleavable by acid, for example, t-butoxycarbonyl or trityl, or also protecting groups which are cleavable by basic hydrolysis, such as trifluoroacetyl, or by protecting groups which are cleavable with thiourea, such as chloro-, bromo- and iodoacetyl. Carboxy groups can be protected by, for example, benzhydryl, t-butyl, allyl or trimethylsilyl groups.

In accordance with process variant (a), a compound of formula III is acylated. As acylating agents, the following are suitable: corresponding carboxylic acids in the presence of 2-halopyridinium salts, for example, of 2-chloro- or 2-fluoro-1-methylpyridinium chloride or tosylate, or also in the presence of N,N-dicyclohexylcarbodiimide, preferably together with N-hydroxybenztriazole or N-hydroxy-succinimide. There can also be used corresponding reactive derivatives of the carboxylic acid, such as the acid halide, acid anhydride or acid azide. Also usable are the corresponding thiolesters, such as 2-benzthiazolyl thioester, as well as hydroxybenztriazole esters or N-hydroxysuccinimide esters. Suitable ester protecting groups for use in the compounds of formula III are, for example, benzhydryl, t-butyl, allyl or trimethylsilyl groups. The reaction is preferably carried out in an organic solvent or solvent mixture, optionally admixture with water, for example, acetone, methylene chloride, dimethylacetamide, dimethylformamide or acetonitrile, optionally in admixture with water. The reaction generally is between −30° C. and room temperature.

In accordance with process variant (b), a compound of formula IV is thiolated with a compound of formula V. As suitable ester protecting groups there can be used the same ones given above for the compounds of formula III. Leaving groups Y are, illustratively, halogens, for example, iodine, acyloxy residues, for example, lower alkanoyloxy- residues such as acetoxy, lower alkyl- or arylsulphonyloxy residues such as mesyloxy or tosyloxy. Preferably, acetoxy is used as leaving group Y. The reaction can be carried out at a temperature between about 40° and 80° C., preferably at about 60° C., in water or in a buffer solution having a pH of about 6-7. Where Y is a halogen atom, M in formula IV should be an ester-protecting group, with the reaction being preferably carried out in a polar organic solvent, for example, in dimethylformamide, ethyl acetate, acetonitrile or tetrahydrofuran. The temperature preferably is between −30° C. and room temperature.

In accordance with process variant (c), a ketocephalosporin of formula VI is reacted with a salt of an O-substituted hydroxylamine of formula VII. Preferred as the salt is a mineral acid salt, for example, the hydrochloride, or an organic sulphonate such as, for example, the p-toluenesulphonate. The salt is preferably used in about an equimolar amount up to a slight excess. The reaction is preferably carried out in a polar organic solvent, for example, in dimethylformamide, N-methylpyrrolidone, dimethyl sulphoxide, acetonitrile, water or, especially, in dimethylacetamide. When the latter solvent is used, there are obtained especially high amounts of the syn-form of the end product. The temperature preferably is between 0° C. and room temperature.

Any protecting groups in the obtained compound, for example, on phenolic hydroxy or amino, can be cleaved off. Phenolic hydroxy protecting groups can be cleaved as follows: acetyl with water at pH 7-8 or with ammonia, trimethylsilyl with ethanol or water, tetrahydropyranyl by acidic hydrolysis, for example, with aqueous hydrochloric acid. Amino protecting groups can be cleaved off as follows: those which are cleavable by acid are preferably removed with the aid of a lower alkanecarboxylic acid which can be optionally halogenated; in particular, formic acid or trifluoroacetic acid is used. Protecting groups which are cleavable by alkali are generally hydrolyzed with dilute aqueous caustic alkali at 0° C. to 30° C. The chloroacetyl, bromoacetyl and iodoacetyl protecting groups can be cleaved off by means of thiourea in an acidic, neutral or alkaline medium at about 0°-30° C.

Any carboxy protecting groups can be cleaved off as follows: when the protecting group represents a trimethylsilyl group, this group can be removed especially readily by treatment with water or ethanol. Benzhydryl and t-butyl groups can be cleaved off with formic acid or trifluoroacetic acid. In general, the temperature is room temperature, although slightly elevated or slightly lowered temperature can be used, for example, in the range of about 0° C. to 40° C. Allyl groups are removed by means of palladium salts and tertiary amines such as N-methylpyrrolidine or N-methylmorpholine.

For the preparation of the readily hydrolyzable esters of the carboxylic acids of formula I in accordance with process variant (e), the carboxylic acid is preferably reacted with the halide, preferably with the iodide, containing the ester group. The reaction can be accelerated with the aid of a base, for example, an alkali metal hydroxide or carbonate or an organic amine such as triethylamine. This reaction is preferably carried out in an inert organic solvent such as dimethylacetamide, hexamethylphosphoric acid triamide, dimethyl sulphoxide or, preferably, dimethylformamide. The temperature preferably is in the range of about 0° to 40° C.

The preparation of the salts and hydrates of the compounds of formula I or of the hydrates of these salts can be effected by reacting the carboxylic acid of formula I with an equivalent amount of the desired base, conveniently in a solvent such as water or in an organic solvent such as ethanol, methanol, acetone or others. Corresponding salt formation is brought about by the addition of an organic or inorganic acid. The temperature of the salt formation generally is room temperature, but different temperatures are also possible, for example, those in the range of from 0° C. to 50° C.

The hydrates are produced, for the most part, automatically in the course of the preparation procedure or as a consequence of hygroscopic properties of an initially anhydrous product. For the planned preparation of a hydrate, a completely or partially anhydrous product (carboxylic acid of formula I or ester or salt thereof) can be exposed to a moist atmosphere, e.g., at about 10° C. to 40° C.

The starting compounds of formula III can be prepared by thiolation in analogy to the above reaction of the compounds IV and V. The same applies to the preparation of the starting compounds of formula VI.

The thiols of formula V are novel compounds. Corresponding carbamoyl derivatives [$R^1$=a group (a)-(d)] can be prepared from the corresponding esters, for example, the 2-(lower alkoxycarbonyl)-s-triazolo[1,5-a]pyrimidine-7-thiols (See Eur. Pat. Publ. 150,507) or the 3-(lower alkoxycarbonyl)-pyrazolo[1,5-a]pyrimidine-7-thiols (See J. Med. Chem. 1981, 24(5), 610-13, or from analogous esters by aminolysis with ammonia or the corresponding amine, or from the corresponding carboxylic acids in the presence of 2-halopyridinium salts, for example, of 2-chloro- or 2-fluoro-1-methylpyridinium chloride or tosylate, or also in the presence of dicyclohexylcarbodiimide, preferably together with N-hydroxybenztriazole or N-hydroxysuccinimide; or also from the corresponding acid chloride with ammonia or the corresponding amine. The preparation of corresponding 5-thiols may be effected starting from a correspondingly substituted 5-amino-s-triazole, which is converted with a ω,ω,ω-trifluoroacetic acid ester or with diketene, followed by a dehydrating agent such as concentrated. sulphuric acid or polyphosphoric acid into the corresponding 5-hydroxy-s-triazolo(or pyrazolo)[1,5-a]pyrimidine. Further processing to the desired 5-thiol is effected by analogy to the synthesis of the 7-thiols which is described in J. Med. Chem. 1981, 24, 610-613, the disclosure of which is incorporated herein by reference.

A syn/anti mixture of a compound of formula I which may be obtained can be separated into the corresponding syn and anti forms in the usual manner, for example, by recrystallization or by chromatographic methods using a suitable solvent or solvent mixture.

The compounds of formula I as well as the corresponding readily hydrolyzable esters and salts and, respectively, the hydrates of these products have antibiotic, especially bactericidal, activity. They have a broad spectrum of activity against Gram-positive and Gram-negative microorganisms, including Staphylococci and various cephalosporin-resistant Gram-negative bacteria such as, for example, Pseudomonas aeruginosa, Enterobacter cloacae, Escherichia coli, Serratia marcescens, Proteus and Klebsiella species.

The compounds of formula I as well as the corresponding readily hydrolyzable esters and salts and, respectively, the hydrates of these products can be used for the treatment and prophylaxis of infectious diseases. In general, a daily dosage of about 0.1 to about 4 grams is suitable for adults. The parenteral administration of the compounds in accordance with the invention is especially preferred.

In order to demonstrate the antimicrobial activity of the mentioned products, various end products prepared in accordance with the working Examples hereinafter were tested in vivo for their activity. The minimal inhibitory concentration in micrograms per milliliter (μg/ml) was measured, and the results are set forth in the following Table, where reference is made to the numbers of the corresponding working Examples.

TABLE

| Organism | End product from Example No. | | | | |
|---|---|---|---|---|---|
|  | 1a | 1b | 1c | 2 | 3 |
| S. aureus 6538 | 1 | 2 | 4 | 8 | 8 |
| E. coli 25922 | 0.25 | 4 | 0.5 | 0.5 | 1 |
| E. coli TEM 1 | <0.06 | 0.5 | 0.25 | 0.25 | 0.5 |
| K. pneumoniae 418 | 0.5 | 4 | 1 | 0.5 | 1 |
| K. oxytoca 1082 E | 4 | 16 | 8 | 2 | 2 |
| E. cloacae P 99 | 16 | 32 | 32 | 16 | 32 |
| P. vulgaris 1028 | 0.5 | 4 | 1 | <0.06 | 0.25 |
| P. aeruginosa 143811S | >32 | >32 | 32 | 16 | 8 |
| P. aeruginosa 143811R | >32 | >32 | 32 | 16 | 8 |
| S. pyogenes β 15 | <0.06 | <0.06 | <0.06 | 0.25 | 0.25 |
| S. marcescens 69438 | 4 | 32 | 4 | 1 | 2 |

The products in accordance with the invention can be used as medicaments, for example, in the form pharmaceutical preparations which contain the described compounds of the invention or their salts in admixture with a pharmaceutical, organic or inorganic inert carrier material suitable for enternal or parenteral administration, such as water, gelatine, gum arabic, lactose, starch, magnesium stearate, talc, vegetable oils, polyalkylene glycols, Vaseline, and so forth. The pharmaceutical preparations can be present in solid form, for example, as tablets, dragees, suppositories, capsules, or in liquid form, for example, as solutions, suspensions or emulsions. If desired, they are sterilized and/or contain adjuvants such as preserving, stabilizing, wetting or emulsifying agents, salts for varying the osmotic pressure, anaesthetics or buffers. They can also contain still other therapeutically valuable substances. The compounds of formula I and their salts and, respectively, hydrates are suitable for parenteral administration and, for this purpose, are preferably prepared as lyophilizates or dry powders for dilution with usual agents such as water or isotonic saline. The readily hydrolyzable esters of the compounds of formula I and their salts and, respectively, hydrates also are useful for enteral administration.

In the following Examples all temperatures are given in degrees Celsius.

EXAMPLE 1 a) 1.37 g of (6R,7R)-7-amino-3-[[(2-carbamoyl-5-methyl-s-triazolo [1,5-a]pyrimidin-7-yl)thio]methyl]-8-oxo-5-thia-1-azabicyclo [4.2.0]oct-2-ene-2-carboxylic acid were suspended in 10 ml of methylene chloride and treated with 2.44 ml of bistrimethylsilylacetamide. After all had passed into solution 1.16 g of 2-(2-amino-4-thiazolyl)-2-(Z)-methoxyimino-acetic acid-2-benzthiazolyl thioester were added and the reaction mixture was stirred at room temperature for 1 hour. 30 ml of methylene chloride were added and the product was precipitated by the dropwise addition of 2 ml of alcohol. The precipitate was filtered off under suction, dried and dissolved in 10 ml of dimethylformamide. 1.6 ml of 2N aqueous Na 2-ethylcaproate was added and the resulting solution was introduced dropwise into 150 ml of ether. The precipitated product was filtered off under suction and dried. There was obtained (6R,7R)-7-[(Z)-2-(2-amino-4-thiazolyl)-2-(methoxyimino)acetamido]-3-[[[2-carbamoyl-5-methyl-s-triazolo[1,5-a]pyrimidin-7-yl]thio]methyl]-8-oxo-5-thia-1-azabicyclo[4.2.0]oct-2-ene-2-carboxylic acid sodium salt.

¹NMR (DMSO-d₆): δ 2.60 (s,3H); 3.52 (d,J=18 Hz,1H); 3.73 (d,J=18 Hz,1H); 3.82 (s,3H); 4.42 (d,J=14 Hz,1H); 4.53 (d,J=14 Hz,1H); 5.13 (d,J=5 Hz,1H); 5.74 (dd,J=8 Hz and J=5 Hz,1H); 6.73 (s,1H); 7.24 (s,2H); 7.56 (s,1H); 7.87 (s,1H); 8.17 (s,1H); 8.61 (d,J=8 Hz,1H) ppm IR (KBr): 1773.

MS (70 eV): 605 (M+H)⁺.

The (6R,7R)-7-amino-3-[[(2-carbamoyl-5-methyl-s-triazolo [1,5-a]pyrimidin-7-yl)thio]methyl]-8-oxo-5-thia-1-azabicyclo [4.2.0]oct-2-ene-2-carboxylic acid used as the starting compound was prepared as follows:

A suspension of 2.50 g of methyl 7-mercapto-5-methyl-s-triazolo [1,5-a]pyrimidine-2-carboxylate (See Eur. Pat. Publ. 150,507) in 25 ml of 25 percent aqueous ammonia was stirred at room temperature for 6 hours. The mixture was filtered and the solid was dried at 50° in a vacuum. There was obtained 7-mercapto-5-methyl-s-triazolo[1,5-a]pyrimidine-2-carboxamide as a 1:1:1 adduct with water and ammonia.

¹H NMR (DMSO-d₆): δ 2.26 (s 3H); 6.72 (s,1H); 7.17 (s,4H,NH₄⁺); 7.60 (broad s,1H); 7.84 (broad s,1H) ppm.

A mixture of 5.46 g of (7R)-7-aminocephalosporanic acid and 4.85 g of 7-mercapto-5-methyl-s-triazolo[1,5-a]pyrimidine-2-carboxamide ammonium salt was treated while stirring well with 50 ml of a 20 percent solution of boron trifluoride in acetonitrile. The temperature was held below 40° by means of ice-bath cooling. The reaction mixture was stirred at 20° for 1 hour and subsequently diluted with 200 ml of water. There formed a white precipitate which was collected by filtration. The still moist material was dissolved in 50 ml of 3N HCl and the solution was filtered. A white product crystallized out from the filtrate after a short time. By filtration, washing with H₂O and acetone and drying in a vacuum there was obtained (6R,7R)-7-amino-3-[[(2-carbamoyl-5-methyl-s-triazolo [1,5-a]pyrimidin-7-yl)-thio]methyl]-8-oxo-5-thia-1-azabicyclo [4.2.0]oct-2-ene-2-carboxylic acid as the hydrochloride.

¹H NMR (DMSO-d₆): δ 2.61 (s,3H); 3.74 (d,J=17.5 Hz,1H); 2.87 (d,J=17.5 Hz,1H); 4.46 (d,J=12.5 Hz,1H); 4.54 (d,J-12.5 Hz,1H); 5.20 (d,J=5 Hz,1H); 5.25 (d,J=5 Hz,1H); 7.43 (s,1H); 7.89 (s,1H); 8.19 (s,1H) ppm.

MS: 422 (M+H)⁺

IR (KBr): 1770.

By analogy to the above method there were prepared the following compounds:

b) (6R,7R)-7-[(Z)-2-(2-Amino-4-thiazolyl)-2-[(pivaloyloxy)imino]acetamido]-3-[[[2-carbamoyl-5-methyl-s-triazolo[1,5-a]pyrimidin-7-yl]thio]methyl]-8- oxo-5-thia-1-azabicyclo [4.2.0]oct-2-ene-2-carboxylic acid sodium salt.

¹H NMR (DMSO-d₆): δ 1.19 (s,9H); 2.58 (s,3H); 3.40 (d,J=18 Hz,1H); 3.61 (d,J=18 Hz,1H); 4.48 (d,J=14 Hz,1H); 4.66 (d,J=14 Hz,1H); 5.07 (d,J=5 Hz,1H); 5.65 (dd,J=8 Hz and J=5 Hz,1H); 6.98 (s,1H); 7.37 (s,2H); 7.86 (2s,2H); 8.17 (s,1H); 9.84 (d,J=8 Hz,1H) ppm.

IR (KBr): 1761.

c) (6R,7R)-7-[(Z)-2-(2-Amino-4-thiazolyl)-2-[(carbamoylmethoxy)imino]acetamido]-3-[[(2-carbamoyl-5-methyl-s-triazolo [1,5-a]pyrimidin-7-yl)thio]methyl]-8-oxo-5-thia-1-azabicyclo [4.2.0]oct-2-ene-2-carboxylic acid sodium salt.

¹H NMR (DMSO-d₆): δ 2.59 (s,3H); 3.42 (d,J=18 Hz,1H); 3.62 (d,J=18 Hz,1H); 4.40 (s,2H); 4.42 (d,J=14 Hz,1H); 4.70 (d,J=14 Hz,1H); 5.05 (d,J=5 Hz,1H); 5.66 (dd,J=8 Hz and J=5 Hz,1H); 6.80 (s,1H); 7.12 (s,1H); 7.38 (s,2H); 7.50 (s,1H); 7.85 (s,2H); 8.24 (s,1H); 9.82 (d,j=8 Hz,1H) ppm.

IR (KBr): 1763.

d) (6R,7R)-7-[(Z)-2-(2-Amino-4-thiazolyl)-2-[[1-(t-butoxycarbonyl) -1-methylethoxy]imino]acetamido]-3-[[[2-carbamoyl-5-methyl-s-triazolo [1,5-a]pyrimidin-7-yl]thio]methyl]-8-oxo-5-thia-1-azabicyclo [4.2.0]oct-2-ene-2carboxylic acid sodium salt.

¹H-NMR (DMSO-d₆): δ 1.38 (s,9H); 1.40 (s,3H); 1.42 (s,3H); 2.61 (s,3H); 3.58 (d,J=18 Hz,1H); 3.80 (d,J=18 Hz,1H); 4.43 (m,2H); 5.20 (d,J=5 Hz,1H); 5.84 (dd,J=8 Hz and J=5 Hz,1H); 6.70 (s,1H); 7.27 (s,broad 2H); 7.42 (s,1H); 7.88 (s,1H); 8.17 (s,1H); 9.42 (d,J=8 Hz,1H) ppm.

IR (KBr): 1773

MS: 733 (M+H)+.

e) (6R,7R)-7-[(Z)-2-(2-Amino-4-thiazolyl)-2-[[(t-butoxycarbonyl)methoxy]imino]acetamido]-3-[[[2-carbamoyl-5-methyl-s-triazolo [1,5-a]pyrimidin-7-yl]thio]methyl]-8-oxo-5-thia-1-azabicyclo [4.2.0]oct-2-ene-2-carboxylic acid sodium salts.

¹H-NMR (DMSO-d₆): δ 1.41 (s,9H); 2.61 (s,3H); 3.58 (d,J=18 Hz,1H); 3.81 (d,J=18 Hz,1H); 4.42 (m,2H); 4.54 (s,2H); 5.20 (d,J=5 Hz,1H); 5.82 (dd,J=8 Hz and J=5 Hz,1H); 6.78 (s,1H); 7.27 (s,broad, 2H); 7.41 (s,1H); 7.88 (s,1H); 8.17 (s,1H); 9.57 (d,J=8 Hz,1H) ppm.

IR (KBr): 1771.

MS: 705 (M+H)+.

EXAMPLE 2

740 mg of (6R,7R)-7-[(Z)-2-(2-amino-4-thiazolyl)-2-[[(t-butoxycarbonyl) methoxy]imino]acetamido]-3-[[[2-carbamoyl-5-methyl-s-triazolo [1,5-a]pyrimidin-7-yl]thio]methyl]-8-oxo-5-thia-1-azabicyclo [4.2.0]oct-2-ene-2-carboxylic acid sodium salt were dissolved in 5 ml of trifluoroacetic acid and stirred at room temperature for 1 hour. The reaction mixture was concentrated in a vacuum and the residue was taken up in ethyl acetate. The resulting white precipitate was filtered off and dried. There was obtained 680 mg of (6R,7R)-7-[(Z)-2-(2-amino-4-thiazolyl)-2-[[(carboxymethoxy)imino]acetamido]-33-[(2-carbamoyl-5-methyl-s-triazolo [1,5-a]pyrimidin-7-yl)thio]methyl]-8-oxo-5-thia-1-azabicyclo[4.2.0]oct-2-ene-2-carboxylic acid trifluoroacetate as a white powder.

EXAMPLE 3

1.56 g of (6R,7R)-7-[(Z)-2-(2-amino-4-thiazolyl)-2-[[1-(t-butoxycarbonyl) -1-methylethoxy]imino]acetamido]-3-[[[2-carbamoyl-5-methyl-s-triazolo[1,5-a]pyrimidin-7-yl]thio]methyl]-8-oxo-5-thia-1-azabicyclo[4.2.0]oct-2-ene-2-carboxylic acid was dissolved in 10 ml of trifluoroacetic acid and stirred at room temperature for 1 hour. The reaction mixture was concentrated in a vacuum and taken up in ethyl acetate. The white precipitate obtained was filtered off and dried. There was obtained (6R,7R)-7-[(Z)-2-(2-amino-4-thiazolyl)-2-[1-(carboxy-1-methylethoxy)imino]acetamido]-3-[[[2-carbamoyl-5-methyl-s-triazolo[1,5-a]pyrimidin-7-yl]thio]methyl]-8-oxo-5-thia-1-azabicyclo[4.2.0]oct-2-ene-2-carboxylic acid trifluoroacetate as a white powder.

EXAMPLE 4

0.228 g (0.4 mmol) of (6R,7R)-7-(2-amino-4-thiazoleglyoxylamido)-3-[[(2-carbamoyl -5-methyl-s-triazolo[1,5-a]pyrimidin-7-yl)thio]methyl]-8-oxo-5-thia-1-azabicyclo [4.2.0]oct-2-ene-2-carboxylic acid was dissolved in 2 ml of dimethylacetamide. 0.140 g (0.52 mmol) of 1-[2-(aminooxy)-2-methylpropionyl]-2-[(1,4-dihydro-5-hydroxy-4-oxo-2-pyridyl) carbonyl]hydrazine and 0.100 g (0.52 mmol) of p-toluenesulfonic acid hydrate were added. After stirring for 20 hours at room temperature the dimethylacetamide was evaporated off at strongly reduced pressure and the residue was taken up in water and stirred for 15 minutes in order to completely precipitate the product. The product was filtered off, washed well with water and dried under strongly reduced pressure at room temperature. (6R,7R)-7-[(Z)-2-(2-amino-4-thiazolyl)-2-[[1,4-dihydro-5-hydroxy -4-oxo-2-pyridyl)carbonyl]carbazoyl]-1-methylethoxy]imino]-acetamido]-3-[[[2-carbamoyl-5-methyl-s-triazolo[1,5-a]-pyrimidin-7-yl) thio]methyl]-8-oxo-5-thia-1-azabicyclo[4.2.0]oct-2-ene-2-carboxylic acid was obtained as beige-colored powder.

¹H-NMR (DMSO-d₆): δ 1,46 (s,3H), 1,49 (s,3H), 2,61 (s,3H); 3,65 (d,J=18 Hz, 1H); 3,86 (d,J=18 Hz, 1H); 4,37 (d,J=14 Hz, 1H); 4,47 (d,J=14 Hz, 1H); 5,24 (d,J=5 Hz, 1H); 5,91 (dd,J=8 Hz und J=5 Hz, 1H); 6,90 (s,1H); 7,37 (s,4H, broad); 7,99 (s,2H, broad); 8,19 (s,1H); 9,30 (s,1H); 9,65 (d,J=8 Hz, 1H).

The (6R,7R)-7-(2-amino-4-thiazoleglyoxylamido)-3-[[(2-carbamoyl -5-methyl-s-triazolo[1,5-a]pyrimidin-7-yl)thio]methyl]-8-oxo-5-thia-1-azabicyclo[4.2.0]oct-2-ene-2-carboxylic acid used as starting compound was prepared as follows:

A suspension of 2.50 g of methyl 7-mercapto-5-methyl-s-triazolo[1,5-a]pyrimidine-2-carboxylate in 25 ml of 25 percent aqueous ammonia was stirred at room temperature for 6 hours. The mixture was filtered and the solid is dried at 50° in a vacuum. There was obtained 7-mercapto-5-methyl-s-triazolo[1,5-a]pyrimidine-2-carboxamide as a 1:1:1 adduct with water and ammonia.

¹H NMR (DMSO-d₆): δ 2.26 (s,3H); 6.72 (s,1H); 7.17 (s,4H, NH₄+); 7.60 (broad s,1H); 7.84 (broad s,1H) ppm.

A mixture of 5.46 g of (7R)-7-aminocephalosporanic acid and 4.85 g of 7-mercapto-5-methyl-s-triazolo[1,5-a]pyrimidine-2-carboxamide was treated while stirring well with 50 ml of 20 percent solution of boron trifluoride in acetonitrile. The temperature was held below 40° by means of ice-bath cooling. The reaction mixture was stirred at 20° for 1 hour and subsequently diluted with 200 ml of water. A white precipitate formed, which was collected by filtration. The still moist material was dissolved in 50 ml of 3N HCl and the solution was filtered. A white product crystallized out from the filtrate after a short period. By filtration, washing with H₂O and acetone and drying in a vacuum there was obtained (6R,7R)-7-amino-3-[[(2-carbomoyl -5-methyls-triazolo[1,5-a]pyrimidin-7-yl)thio]-methyl]-8-oxo-5-thia-1-azabicyclo[4.2.0]oct-2-ene-2-carboxylic acid as the hydrochloride. $^1$H NMR (DMSO-d$_6$): δ 2.61 (s,3H); 3.74 (d,J=17.5 Hz,1H); 2.87 (d,J=17.5 Hz,1H); 4.46 (d,J=12.5 Hz,1H); 4.54 (d,J=12.5 Hz,1H); 5.20 (d,J=5 Hz,1H); 5.25 (d,J=5 Hz,1H); 7.43 (s,1H); 7.89 (s,1H); 8.19 (s,1H) ppm.

MS: 422 (M+H$^+$).

IR (KBr): 1770.

A suspension of 1.71 g of (6R,7R)-7-amino-3-[[(2-carbamoyl -5-methyl-s-triazolo[1,5-a]pyrimidin-7-yl)thio]-methyl]-8-oxo-5-thia-1-azabicyclo[4.2.0]oct-2-ene-2-carboxylic acid hydrochloride in 20 ml of methylene chloride was treated with 2.74 ml of N,O-bis-(trimethylsilyl)acetamide. After all had passed into solution 1.32 g of 2-amino-4-thiazolethioglyoxylic acid s-(2-benzothiazolyl) ester was added and the mixture was stirred at 20° for 1.5 hours. Undissolved material was separated by filtration and the filtrate was diluted with 40 ml of methylene chloride. Upon the dropwise addition of 2 ml of ethanol there resulted a yellow precipitate which was collected by filtration and dried in a vacuum. There was obtained (6R,7R)-7-(2-amino-4-thiazoleglyoxylamido)-3-[[(2-carbamoyl -5-methyl-s-triazolo[1,5-a]pyrimidin-7-yl)thio]methyl]-8-oxo-5-thia-1-azabicyclo[4.2.0]oct-2-ene-2-carboxylic acid as a yellow powder.

$^1$H NMR (DMSO-d$_6$): δ 2.60 (s,3H); 3.54 (d,J=17.5 Hz,1H); 3.74 (d,J=17.5 Hz,1H); 4.42 (d,J=14 Hz,1H); 4.56 (d,J=14 Hz,1H); 5.14 (d,J=5 Hz,1H); 5.72 (d,J=5 Hz,1H); 7.41 (s,2H); 7.55 (s,1H) ppm.

The 1-[2-(aminooxy)-2-methylpropionyl]-2-[(1,4-dihydro -5-hydroxy-4-oxo-2-pyridyl)carbonyl]hydrazine used as starting material was prepared as follows:

1.20 g (7.1 mmol) of (1,4-Dihydro-5-hydroxy-4-oxo-2-pyridyl)carbonylhydrazine was dissolved in 120 ml of acetonitrile. After the addition of 2.88 g (14.1 mmol) of bis(trimethylsilyl)acetamide the mixture was stirred for 2 hours at 90°. The solution was cooled to room temperature and treated with 2.83 g (7.1 mmol) of 2-methyl-2-(phthalimidooxy)-propionic acid-2-benzothiazole thiol ester. After stirring for 20 hours the solution was evaporated under reduced pressure at room temperature. The residue was taken up in 180 ml of ethanol and boiled under reflux conditions for 7 minutes. Undissolved material was filtered off and the filtrate was concentrated. After the addition of ether the product crystallized. 1-[(1,4-Dihydro-5-hydroxy-5-oxo-2-pyridyl) carbonyl]-2-[2-methyl-2-(phthalimidooxy)propionyl]hydrazine was obtained as white crystals melting at 239°-241°.

0.670 g (1.675 mmol) of 1-[(1,4-dihydro-5-hydroxy-4-oxo-2-pyridyl)carbonyl]-2-[2-methyl-2-(phthalimidooxy)propionyl]hydrazine was dissolved in 1.5 ml of dimethylformamide and treated with 0.077 g (1.675 mmol) of methylhydrazine. After stirring for 2½ hours at room temperature about 2 ml of ethanol were added. The crystals obtained were filtered off and discarded. The filtrate was evaporated under strongly reduced pressure and the product was crystallized from ethanol. 1-[2-(aminooxy)-2-methylpropionyl]-2-[(1,4-dihydro-5-hydroxy-4-oxo-2-pyridyl)carbonyl]hydrazine was obtained as white crystals melting at 234° (dec.).

EXAMPLES 5

0.230 g (0.4 mmol) of (6R,7R)-7-(2-amino-4-thiazoleglyoxylamido) -3-[[(2-carbamoyl-5-methyl-s-triazolo[1,5-a]pyrimidin-7-yl)thio]methyl]-8-oxo-5-thia-1-azabicyclo[4.2.0] oct-2-ene-2-carboxylic acid was dissolved in 3.5 ml of dimethylacetamide. Within 6 hours 0.11 g (0.7 mmol) of 2-(aminooxy)methyl-5-hydroxy-4(1H)-pyrimidinone and 0.133 g (0.7 mmol) of p-toluenesulfonic acid hydrate were added. After further stirring for 18 hours the dimethylacetamide was evaporated off at strongly reduced pressure, and the residue was taken up in water and stirred for 20 minutes in order to completely precipitate the product. The product was filtered off, washed well with water and dried under strongly reduced pressure at room temperature. (6R,7R)-7-[(Z)-2-(2-amino-4-thiazolyl)-2-[[(1,4-dihydro -5-hydroxy-4-oxo-2-pyrimidinyl) methoxy]imino]-acetamido]-3-[[(2-carbamoyl -5-methyl-s-triazolo[1,5-a]pyrimidin-7-yl)thio]methyl]-8-oxo-5-thia-1-azabicyclo[4.2.0]oct-2-ene-2-carboxylic acid was obtained as a beige powder.

$^1$H-NMR (DMSO-d$_6$): δ 2,61 (s,3H); 3,53 (d,J=18 Hz,1H); 3,82 (d,J=18 Hz,1H); 4,38 (d,J=14 Hz,1H); 4,46 (d,J=14 Hz,1H); 4,92 (s, breit, 2H); 5,20 (d,J=5 Hz, 1H); 5,86 (dd,J=8 Hz und J=5 Hz,1H); 6,87 (s,1H); 7,38 (s,1H); 7,39 (s, broad, 3H); 7,88 (s,1H); 8,18 (s,1H); 9,93 (d,J=8 Hz,1H).

The 2-(aminooxy)methyl-5-hydroxy-4(1H)-pyrimidinone used as the starting material was prepared as follows:

0.696 g (3 mmol) of 5-hydroxy-2-hydroxymethyl-4(1H)-pyrimidinone, 0.787 g (3 mmol) of triphenylphosphine and 0.489 g (3 mmol) of N-hydroxyphthalimide were dissolved in 50 ml of dimethylacetamide. At 20° a solution of 0.640 g (3.3 mmol) of azodicarboxylic acid diethyl ester in 2 ml of dimethylacetamide was added dropwise to said mixture. The mixture so obtained was stirred for 20 hours at room temperature and the solvent was evaporated off under strongly reduced pressure. The residual yellow oil was crystallized from ethanol/ether. After recrystallization from ethanol, 4-[(5-benzyloxy)-1,4-dihydro-4-oxo-2-pyrimidinyl]methoxy]phthalimide was obtained as white crystals melting at 157°.

0.754 g 2 mmol) of N-[(5-benzyloxy)-1,4-dihydro-4-oxo-2-pyrimidinyl]methoxy]phthalimide was suspended in 60 ml of methylenechloride and treated dropwise at −70° C. with 560 mg (2.2 mmol) of boron tribromide. After stirring for 4 hours at −70° the mixture was warmed to room temperature and further stirred for 16 hours. The solvent was evaporated off under reduced pressure, and the residue was treated with 30 ml of water and stirred. The product was filtered off, washed with water and ether and dried under strongly reduced pressure at 35°. 5-Hydroxy-2-phthalimi-dooxy)methyl]-4(1H)-pyrimidinone was obtained as white crystals melting at 174°-175°.

0.875 g (3 mmol) of 5-hydroxy-2-phthalimidooxymethyl]-4(1H)-pyrimidinone was suspended in 7 ml of dimethylformamide. The suspension was treated at 10° with 136 mg (3 mmol) of methylhydrazine and stirred 1 hour at room temperature. The solution was washed four times with 50 ml of n-pentane and the solid residue taken up in ether, the product was filtered off and crystallized from ethanol. 2-(Aminooxy)-methyl-5-hydroxy-4-(1H)-pyrimidinone was obtained as white crystals melting at 163°.

EXAMPLE 6

Preparation of Dry Ampoules for Intramuscular Administration

A lyophilizate of 1 g of the sodium salt of (6R,7R)-7-(Z)-2-(2-amino -4-thiazolyl)-2-(methoxyimino]acetamido]-3-[[[2-carbamoyl-5-methyl-s-triazolo [1,5-a]pyrimidin-7-yl]thio]-methyl]-8-oxo-5-thia-1-azabicyclo[4.2.0]oct-2-ene-2-carboxylic acid is prepared in the usual manner and filled into an ampoule. Prior to the administration the lyophilizate is treated with 2.5 ml of a 2% aqueous lidocaine hydrochloride solution.

We claim:

1. A compound of formula

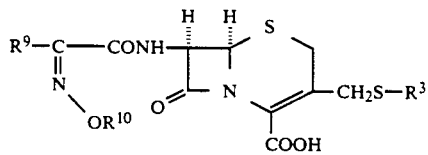

wherein $R^3$ is a substituted bicyclic group of formula:

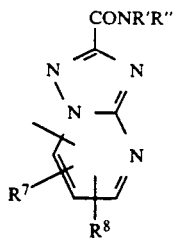

wherein $R^7$ and $R^8$ are independently hydrogen, lower alkyl having 1–7 carbon atoms or trifluoromethyl, or together represent alkylene with 3 or 4 carbon atoms, and $R'$ and $R''$ are independently hydrogen, lower alkyl having 1–7 carbon atoms or lower cycloalkyl having 3–7 carbon atoms, $R^9$ is an unsubstituted or substituted 5- or 6-membered heterocyclic group having 1–4 heteroatoms selected from nitrogen, oxygen and sulfur with the substituents selected from the group consisting of halogen, hydroxy, nitro, amino, cyano, trifluoromethyl, $C_1$–$C_7$ lower alkyl and $C_1$–$C_7$ lower alkoxy, and $R^{10}$ is hydrogen, lower alkanoyl having 1–7 carbon atoms, lower alkyl having 1–7 carbon atoms, lower alkenyl having 1–7 carbon atoms, lower cycloalkyl having 3–7 carbon atoms, lower cycloalkenyl having 3–7 carbon atoms or $C_1$–$C_7$ lower alkyl substituted by carboxy, carbamoyl, lower alkoxycarbonyl having 1–7 carbon atoms, or lower alkanoyl having 1–7 carbon atoms, or $R^{10}$ is a group of formulas

—P—Q

—P—CO—Q

—P—CO—NH—NH—CO—$Q^1$ wherein P is lower alkylene having 1–7 carbon atoms or lower cycloalkylene having 3–7 carbon atoms, Q is one of the groups

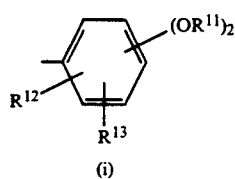

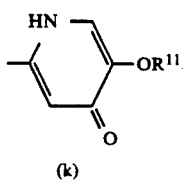

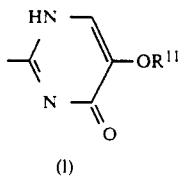

wherein $R^{11}$ is hydrogen, lower alkanoyl having 1–7 carbon atoms or tri($C_1$–$C_7$ lower alkyl)-silyl, $R^{12}$ is hydrogen, —$OR^{11}$, lower alkoxy having 1–7 carbon toms, halogen, —$OCOR^{14}$, —$OCOOR^{14}$, —$N(R^{14})_2$, —NH—$COR^{14}$, —$NHCOOR^{14}$, —$COR^{14}$, —$SR^{14}$, —$SOR^{14}$, —$SO_2R^{14}$, —$SO_3H$, —$COOR^{14}$, —$CON(R^{14})_2$ or nitro, $R^{13}$ is hydrogen or halogen and $R^{14}$ is hydrogen or lower alkyl having 1–7 carbon toms, wherein in (i) the two —$OR^{11}$ groups are present in the 2,3- or 3,4-position; and $Q^1$ is one of the groups (k) and (l), wherein the compounds of formula Ia are present in the syn-isomeric form or as a mixture with the anti-isomeric form in which the syn-isomeric form predominates, or a readily hydrolyzable ester or pharmaceutically acceptable salt of the compound, or a hydrate of the compound or of its ester or salt.

2. A compound according to claim 1, wherein $R^3$ is one of the groups

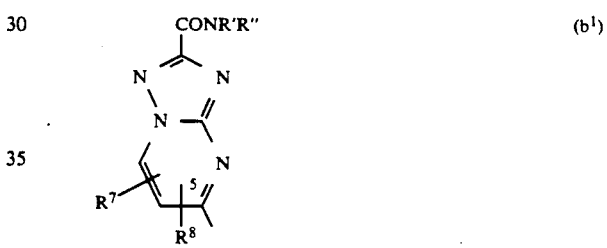

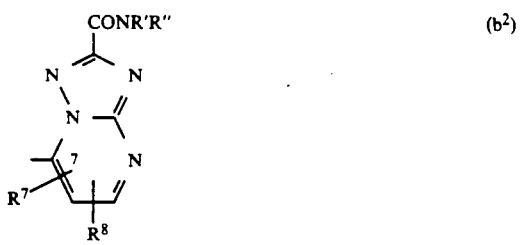

wherein $R'$, $R''$, $R^7$ and $R^8$ are as defined in claim 32.

3. A compound according to claim 1, wherein $R^3$ is a carbamoyl-substituted bicyclic group of the formula

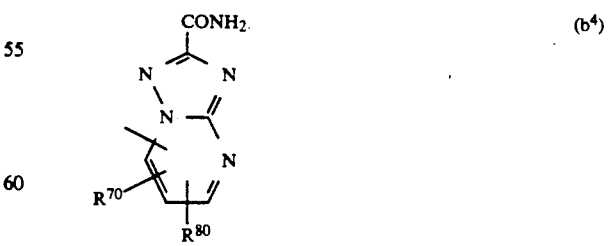

wherein $R^{70}$ and $R^{80}$ are independently hydrogen, methyl or trifluoromethyl or together represent alkylene having 3 or 4 carbon atoms.

4. A compound according to claim 2, wherein $R^3$ is one of the groups

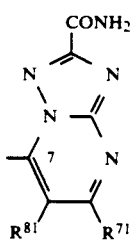
(b⁵)

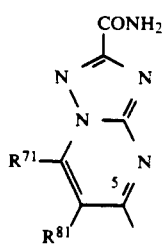
(b⁶)

wherein R⁷¹ is methyl or trifluoromethyl and R⁸¹ is hydrogen or R⁷¹ and R⁸¹ together represent tetramethylene.

5. A compound according to claim 3, wherein R³ is the group (b⁴) which is linked to the rest of the molecule via ring position 5 as follows:

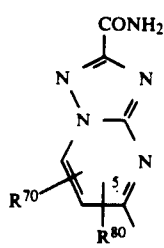

6. A compound according to claim 3, wherein R³ is the group (b⁴) which is linked to the rest of the molecule via ring position 7 as follows:

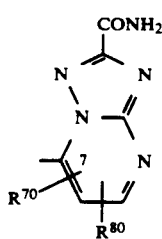

7. A compound according to claim 6, wherein R³ is the group

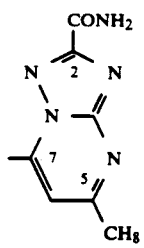
(b⁸)

8. A compound according to claim 1, wherein R⁹ is 2-amino-4-thiazolyl or 5-amino-3-thiadiazolyl.

9. A compound according to claim 1, wherein R¹⁰ is hydrogen, lower alkanoyl having 1-7 carbon atoms, lower alkyl having 1-7 carbon atoms or C₁-C₇ lower alkyl substituted by carboxy, carbamoyl, lower alkoxycarbonyl having 1-7 carbon atoms or lower alkanoyl having 1-7 carbon atoms.

10. A compound according to claim 9, wherein R¹⁰ is methyl, allyl, carboxymethyl, carbamoylmethyl, 1-carboxy-1-methylethyl or pivaloyl.

11. A compound according to claim 1, wherein R¹⁰ is one of the groups

—P¹—Q

—P¹—CO—Q

—P¹—CO—NH—NH—CO—Q¹ wherein Q and Q¹ are as defined in claim 2 and p¹ is the group —CH₂— or

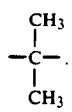

12. A compound according to claim 11, wherein R¹⁰ is one of the groups

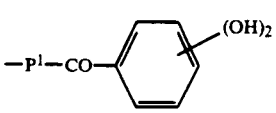

wherein p¹ is as defined in claim 11 and the two hydroxy groups are present in the 2,3- or 3,4-position.

13. A compound according to claim 11, wherein R¹⁰ is one of the groups

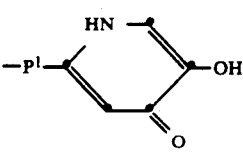

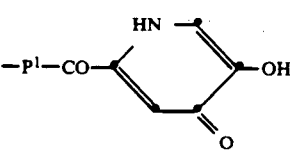

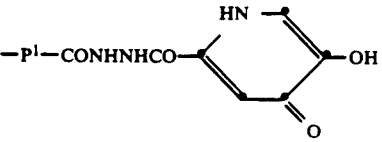

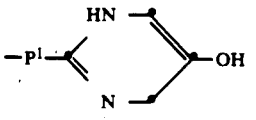

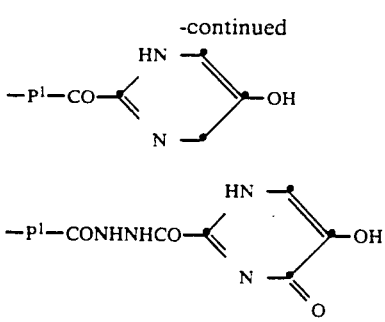

wherein p¹ is as defined in claim 11.

14. A compound according to claim 1, which is selected from the group consisting of:
(6R,7R)-7-[(Z)-2-(2-Amino-4-thiazolyl)-2-(methoxyimino)acetamido]-3-[[[2-carbamoyl-5-methyl-s-triazolo-[1,5-a]pyrimidin-7-yl]thio]methyl]-8-oxo-5-thia-1-azabicyclo[4.2.0]oct-2-ene-2-carboxylic acid,
(6R,7R)-7-[(Z)-2-(2-amino-4-thiazolyl)-2-[[(t-butoxycarbonyl) methoxy]imino]acetamido]-3-[[[2-carbamoyl-5-methyl-s-triazolo[1,5-a]pyrimidin -7-yl]thio]methyl]-8-oxo-5-thia-1-azabicyclo[4.2.0]oct-2-ene-2-carboxylic acid,
(6R,7R)-7-[(Z)-2-(2-amino-4-thiazolyl)-2-[(pivaloyloxy)imino]acetamido]-3-[[[2-carbamoyl-5-methyl-s-triazolo-[1,5-a]pyrimidin-7-yl]thio]methyl]-8-oxo-5-thia-1-azabicyclo[4.2.0]-oct-2-ene-2-carboxylic acid,
(6R,7R)-7-[(Z)-2-(2-amino-4-thiazolyl)-2-[[1-(t-butoxycarbonyl) -1-methylethoxy]imino]acetamido]-3-[[[2-carbamoyl-5-methyl-s-triazolo [11,5-a]pyrimidin-7-yl]thio]methyl]-8-oxo-5-thia -1-azabicyclo[4.2.0]oct-2ene-2-carboxylic acid,
(6R,7R)-7-P(Z)-2-(2-amino-4-thiazolyl)-2-[(carboxymethoxy)-imino]acetamido]-3-[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid,
(6R,7R)-7-[(Z)-2-(2-amino-4-thiazolyl)-2-[1-(carboxy-1-methylethoxy) imino]acetamido]-3-[[[2-carbamoyl-5-methyl-s-triazolo [1,5-a]pyrimidin-7-yl]thio]methyl]-8-oxo-5-thia-1-azabicyclo [4.2.0]oct-2-ene-2-carboxylic acid and
(6R,7R)-7-[(Z)-2-(2-amino-4-thiazolyl)-2-[(carbamoylmethoxy)imino]acetamido]-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid, and a pharmaceutically acceptable of any of the foregoing.

15. A compound according to claim 1, which is selected from the group consisting of:
(6R,7R)-7-[(Z)-2-(2-amino-4-thiazolyl)-2-[[1-[3-[(1,4-dihydro -5-hydroxy-4-oxo-2-pyridyl)carbonyl]carbazoyl]-1-methylethoxy]imino]acetamido]-3-[[(2-carbamoyl-5-methyl-s-triazolo[1,5-a]pyrimidin-7-yl)thio]methyl]-8-oxo-5-thia-1-azabicyclo[4.2.0]oct-2-ene-2-carboxylic acid and
(6R,7R)-7-[(Z)-2-(2-amino-4-thiazolyl)-2-[[(1,4-dihydro-5-hydroxy-4-oxo -2-pyrimidinyl)methoxy]imino]acetamido]-3-[[(2-carbamoyl-5-methyl-s-triazolo [1,5-a]pyrimidin-7-yl)thio]methyl]-8-oxo-5-thia-1-azabicyclo [4.2.0]oct-2-ene-2-carboxylic acid, and a pharmaceutically acceptable salt of any of the foregoing.

16. A pharmaceutical composition comprising an antibacterially effective amount of a compound according to claim 1 and an inert carrier.

17. A pharmaceutical composition according to claim 16 which is in a dosage form suitable for parenteral administration.

18. A pharmaceutical composition according to claim 16 which is in a dosage form suitable for enteral administration.

19. A method of treating a bacterial infection comprising administering to the infected host a therapeutic amount of a pharmaceutical composition according to claim 16.

* * * * *

UNITED STATES PATENT AND TRADEMARK OFFICE
CERTIFICATE OF CORRECTION

PATENT NO. : 5,055,572

DATED : October 8, 1991

INVENTOR(S) : Andre Furlenmeier, et. al.

It is certified that error appears in the above-identified patent and that said Letters Patent is hereby corrected as shown below:

Column 20, line 49, delete "32" and insert therefor -- 1 --.

Column 23, line 35, delete "2ene-2-carboxylic acid," and insert therefor-- 2-ene-2-carboxylic acid, --.

Signed and Sealed this

Twenty-sixth Day of January, 1993

Attest:

STEPHEN G. KUNIN

Attesting Officer

Acting Commissioner of Patents and Trademarks